United States Patent [19]

Wada et al.

[11] Patent Number: 4,889,552
[45] Date of Patent: Dec. 26, 1989

[54] 2-PHENOXYPYRIMIDINE DERIVATIVE AND HERBIDICAL COMPOSITION

[75] Inventors: Nobuhide Wada; Yoshihiro Saito, both of Shizuoka; Shoji Kusano, Hamamatsu; Yasufumi Toyokawa; Takeshige Miyazawa, both of Shizuoka; Satoru Takahashi, Shizuoka, all of Japan

[73] Assignees: Kumiai Chemical Industry Co., Ltd.; Ihara Chemical Industry Co., Ltd., both of Tokyo, Japan

[21] Appl. No.: 181,366

[22] Filed: Apr. 13, 1988

[30] Foreign Application Priority Data

Apr. 14, 1987 [JP] Japan .................................. 62-091787
Apr. 14, 1988 [JP] Japan .................................. 63-091788

[51] Int. Cl.$^4$ .................... A01N 43/54; C07D 239/60
[52] U.S. Cl. .......................................... 71/92; 544/299; 544/301; 544/302; 544/303; 544/304; 544/306
[58] Field of Search .............. 544/299, 301, 302, 303, 544/304, 306; 71/92

[56] References Cited

U.S. PATENT DOCUMENTS

| 4,427,437 | 1/1984 | Serban et al. | 544/299 |
| 4,770,691 | 9/1988 | Zuzu et al. | 544/310 |

FOREIGN PATENT DOCUMENTS

| 15124 | 9/1980 | European Pat. Off. | 544/316 |
| 256985 | 2/1988 | European Pat. Off. | 544/316 |
| 3602016 | 6/1987 | Fed. Rep. of Germany | 544/316 |
| 9474 | 5/1967 | Japan . | |
| 55729 | 5/1979 | Japan . | |
| 117486 | 9/1979 | Japan . | |
| 7046968 | 3/1982 | Japan | 544/316 |

OTHER PUBLICATIONS

Agr. Biol. Chem., vol. 30, No. 9, pp. 896–905, 1966, Jojima et al., "Syntheses and Herbicidal Activities of . . .".
Serban et al., Chem. Abst. 92-175773f (1980).
Kijima et al., Chem. Abst. 93-150268c (1980).
Nezu et al., Chem. Abst. 107-134322t (1987).
Saito et al., Chem. Abst 108-167496b (1988).
Shigematsu et al., Chem. Abst. 108-167509h (1988).

*Primary Examiner*—Mukund J. Shah
*Assistant Examiner*—Cecilia Shen
*Attorney, Agent, or Firm*—Oblon, Spivak, McClelland, Maier & Neustadt

[57] ABSTRACT

A 2-phenoxypyrimidine derivative having the formula:

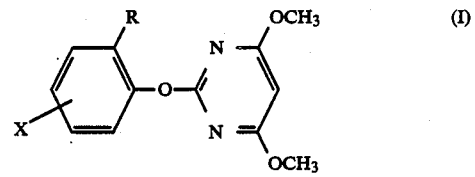

wherein R is a formyl group or —COOR$^1$ wherein R$^1$ is a hydrogen atom, a lower alkyl group, a 2-methylsulfonylethyl group, a diethoxypropyl group, a lower alkenyl group, a lower alkynyl group, a haloalkyl group, a haloalkenyl group, an alkoxyalkyl group, a hydroxyalkyl group, a cycloalkyl group, a phenyl group or

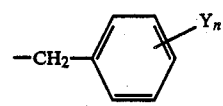

wherein Y is a halogen atom, a methyl group or a methoxy group and n is 0, 1 or 2; and X is a halogen atom, an alkynyloxy group, an alkenyloxy group, an alkylthio group, an alkoxyalkyloxy group, a haloalkoxy group, an acetyloxy group, a benzoyloxy group, a formyl group, a trifluoromethyl group, a carboxyl group, an alkoxycarbonyl group, a dialkylamino group, a dimethoxymethyl group,

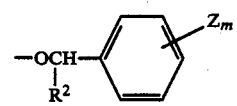

wherein R$^2$ is a hydrogen atom or a methyl group, Z is a chlorine atom or an alkyl group and m is 0, 1 or 2, or

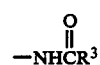

wherein R$^3$ is an alkyl group or a phenyl group, or X forms a methylenedioxy group attached to the adjacent carbon atoms, provided that when X is a halogen atom, it is located at the 6-position of the phenyl group and R is —COOR$^1$ wherein R$^1$ is a lower alkenyl group, a lower alkynyl group, a haloalkyl group, a haloalkenyl group, an alkoxyalkyl group, a hydroxyalkyl group, a cycloalkyl group, a phenyl group or wherein Y is a halogen atom, a methyl group or a methoxy group and n is 1 or 2.

16 Claims, No Drawings

2-PHENOXYPYRIMIDINE DERIVATIVE AND HERBIDICAL COMPOSITION

The present invention relates to novel 2-phenoxypyrimidine derivatives and herbicidal compositions containing them as active ingredients, which are applicable to paddy rice fields, upland fields and non-agricultural fields.

It is disclosed that some 2-phenoxypyrimidine derivatives have herbicidal activities, for instance, in (1) Agr. Biol. Chem. Vol. 30, No. 9, p. 896 (1966), (2) Japanese Unexamined Patent Publication No. 55729/1979, (U.S. Pat. No. 4,427,437) (3) Japanese Unexamined Patent Publication No. 117486/1979 and (4) Japanese Examined Patent Publication No. 9474/1967.

However, the compounds disclosed in such publications and literature have no adequate herbicidal effects against annual weeds, and they exhibit no substantial herbicidal activities against perennial weeds.

The present inventors have conducted extensive research on 2-phenoxypyrimidine compounds with an aim to develop a compound having excellent herbicidal activities and have previously reported some compounds in E.P. 223,406A, 249,707A and 249,708A. As a result of further research, they have now found that the compounds of the present invention with substituents introduced to certain specific positions on the pyrimidine and benzene rings exhibit excellent herbicidal effects not only against annual weeds but also against perennial weeds, particularly against purple nutsedge (*Cyperus rotundus*) and Johnsongrass (*Sorghun halepense*), and at the same time they have a high level of safety against crop plants. The present invention has been accomplished on the basis of these discoveries.

The present invention provides a 2-phenoxypyrimidine derivative having the formula:

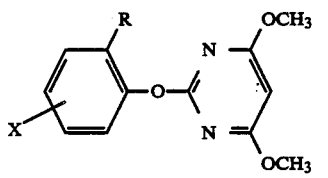

(I)

wherein R is a formyl group or —COOR$^1$ wherein R$^1$ is a hydrogen atom, a lower alkyl group (preferably a C$_1$–C$_{10}$ alkyl group), a 2-methylsulfonylethyl group, a diethoxypropyl group, a lower alkenyl group (preferably a C$_3$–C$_8$ alkenyl group), a lower alkynyl group (preferably a C$_3$–C$_8$ alkynyl group), a haloalkyl group (preferably a C$_2$–C$_8$ haloalkyl group), a haloalkenyl group (preferably a C$_3$–C$_8$ haloalkenyl group), an alkoxyalkyl group (preferably a C$_1$–C$_5$ alkoxy-C$_1$–C$_8$ alkyl group), a hydroxyalkyl group (preferably a C$_2$–C$_8$ hydroxyalkyl group), a cycloalkyl group (preferably a C$_3$–C$_6$ cycloalkyl group), a phenyl group or

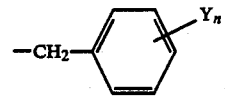

wherein Y is a halogen atom, a methyl group or a methoxy group and n is 0, 1 or 2; and X is a halogen atom, an alkynyloxy group (preferably a C$_3$–C$_6$-alkynyloxy group), an alkenyloxy group (preferably a C$_3$–C$_6$ alkenyloxy group), an alkylthio group (preferably a C$_1$–C$_5$ alkylthio group), an alkoxyalkoxy group (preferably a C$_1$–C$_6$ alkoxy-C$_2$–C$_6$ alkoxy group), a haloalkoxy group (preferably a C$_1$–C$_6$ haloalkoxy group), an acetyloxy group, a benzoyloxy group, a formyl group, a trifluoromethyl group, a carboxyl group, an alkoxycarbonyl group (preferably a C$_1$–C$_6$ alkoxycarbonyl group), a dialkylamino group (preferably a di-C$_1$–C$_5$ alkylamino group), a dimethoxymethyl group,

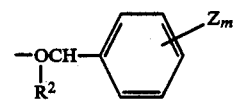

wherein R$^2$ is a hydrogen atom or a methyl group, Z is a chlorine atom or an alkyl group and m is 0, 1 or 2, or

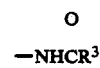

wherein R$^3$ is an alkyl group or a phenyl group or X forms a methylenedioxy group attached to the adjacent carbon atoms, provided that when X is a halogen atom, it is located at the 6-position of the phenyl group and R is —COOR$^1$ wherein R$^1$ is a lower alkenyl group (preferably a C$_3$–C$_8$ alkenyl group), a lower alkynyl group (preferably a C$_3$–C$_8$ alkynyl group), a haloalkyl group (preferably a C$_2$–C$_8$ haloalkyl group), a haloalkenyl group (preferably a C$_3$–C$_8$ haloalkenyl group), an alkoxyalkyl group (preferably a C$_1$–C$_5$ alkoxy-C$_1$–C$_8$ alkyl group), a hydroxyalkyl group (preferably a C$_2$–C$_8$ hydroxyalkyl group), a cycloalkyl group (preferably a C$_3$–C$_6$ cycloalkyl group), a phenyl group or

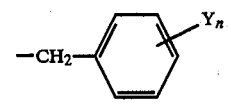

wherein Y is a halogen atom, a methyl group or a methoxy group and n is 1 or 2.

The present invention also provides a herbicidal composition which comprises a herbicidally effective amount of a 2-phenoxypyrimidine derivative of the formula III and an agricultural adjuvant or carrier.

Now, the present invention will be described in detail with reference to the preferred embodiments.

A preferred group of the compounds of the present invention may be represented by the formula:

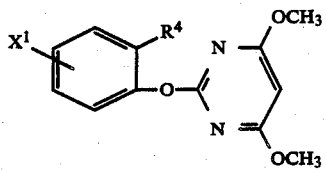

wherein R⁴ is a formyl group or —COOR⁵ wherein R⁵ is a hydrogen atom, a lower alkyl group (preferably a $C_1$–$C_{10}$ alkyl group), a benzyl group which may be substituted by a methoxy group, a 2-methylsulfonylethyl group or a diethoxypropyl group; and $X^1$ is an alkynyloxy group (preferably a $C_3$–$C_6$ alkynyloxy group), an alkenyloxy group (preferably a $C_3$–$C_6$ alkenyloxy group), an alkylthio group (preferably a $C_1$–$C_5$ alkylthio group), an alkoxyalkoxy group (preferably a $C_1$–$C_6$ alkoxy–$C_2$–$C_6$ alkoxy group), a haloalkoxy group (preferably a $C_1$–$C_6$ haloalkoxy group), an acetyloxy group, a benzoyloxy group, a formyl group, a trifluoromethyl group, a carboxyl group, an alkoxycarbonyl group (preferably a $C_1$–$C_6$ alkoxycarbonyl group),

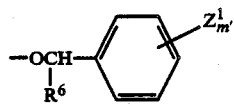

wherein $R^6$ is a hydrogen atom or a ethyl group, $Z^1$ is a chlorine atom or an alkyl group and m' is 0, 1 or 2, a dialkylamino group (preferably a di-$C_1$–$C_5$ alkylamino group),

wherein $R^7$ is an alkyl group or a phenyl group, or a dimethoxymethyl group, or $X^1$ forms a methylenedioxy group attached to the adjacent carbon atoms.

R₄ is preferably a formyl group or —COOR⁵ wherein R⁵ is a hydrogen atom, a lower alkyl group or a benzyl group, particularly preferably a hydrogen atom or a benzyl group.

$X^1$ is preferably a formyl group, an alkynyloxy group, an alkenyloxy group, an alkoxyalkoxy group, a haloalkoxy group, a benzoyloxy group, a trifluoromethyl group, an alkoxycarbonyl group, a dialkylamino group or

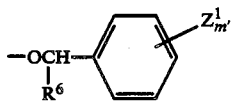

wherein $R^6$ is a hydrogen atom or a methyl group, $Z^1$ is an alkyl group and m' is 0 or 1, or $X^1$ forms a methylenedioxy group attached to the adjacent carbon atoms.

More preferably, $X^1$ is an alkynyloxy group, an alkenyloxy group, an alkoxyalkoxy group, a haloalkoxy group, a trifluoromethyl group, an alkoxycarbonyl group or a benzyloxy group, or $X^1$ forms a methylenedioxy group attached to the two adjacent carbon atoms.

Most preferably, R⁴ is a formyl group or —COOR⁵ wherein R⁵ is a hydrogen atom or a benzyl group, and $X^1$ is a propynyloxy group, a propenyloxy group, an ethoxyethoxy group, a trifluoromethyl group, a difluoromethoxy group, a methoxycarbonyl group or a benzyloxy group, or $X^1$ forms a methylenedioxy group attached to the two adjacent carbon atoms.

Another preferred group of the compounds of the present invention may be presented by the formula:

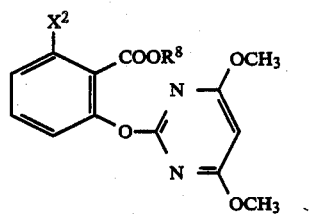

wherein $R^8$ is a lower alkenyl group (preferably a $C_3$–$C_8$ alkenyl group), a lower alkynyl group (preferably a $C_3$–$C_8$ alkynyl group), a haloalkyl group (preferably a $C_2$–$C_8$ haloalkyl group), a haloalkenyl group (preferably a $C_3$–$C_8$ haloalkenyl group), an alkoxyalkyl group (preferably a $C_1$–$C_5$ alkoxy–$C_1$–$C_8$ alkyl group), a hydroxyalkyl group (preferably a $C_2$–$C_8$ hydroxyalkyl group), a cycloalkyl group (preferably a $C_3$–$C_6$ cycloalkyl group), a phenyl group or

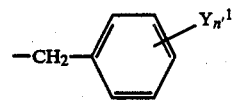

wherein $Y^1$ is a halogen atom, a methyl group or a methoxy group and n' is 1 or 2; and $X^2$ is a halogen atom.

$R^8$ is preferably a lower alkenyl group, a lower alkynyl group, a haloalkyl group, a haloalkenyl group, an alkoxyalkyl group, a phenyl group or

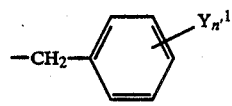

wherein $Y^1$ is a halogen atom or a methoxy group and n' is 1.

More preferably, $R^8$ is an alkoxyalkyl group, a phenyl group or

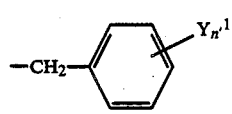

wherein $Y^1$ is a halogen atom or a methoxy group and n' is 1.

Most preferably, $X^2$ is a chlorine atom, and $R^8$ is a methoxymethyl group, a phenyl group, a 3-fluorobenzyl group or a 4-methoxybenzyl group.

Now, specific examples of the compound of the invention will be presented in Table 1. Compound numbers given in the Table will be referred to in the subsequent description in the specification.

TABLE 1

| Compound No. | R | X | Melting point (°C.) or refractive index $n_D^{20}$ |
|---|---|---|---|
| 1 | $CO_2CH_3$ | 3-$CH(OCH_3)_2$ | 85–86 |
| 2 | $CO_2CH_3$ | 6-$CH(OCH_3)_2$ | 83–85 |
| 3 | $CO_2CH_2$—phenyl | 6-$CF_3$ | 78–81 |
| 4 | $CO_2CH_2$—phenyl | 6-$CO_2CH_3$ | 66–67 |
| 5 | COOH | 6-$CO_2CH_3$ | 1.5541 |
| 6 | $CO_2CH_2$—phenyl | 5,6- –O–CH$_2$–O– | 93–95 |
| 7 | COOH | 5,6- –O–CH$_2$–O– | 198–201 |
| 8 | $CO_2CH_2$—phenyl | 6-$NHCOCH_3$ | 1.5720 |
| 9 | COOH | 5-$N(CH_3)_2$ | 200–203 |
| 10 | $CO_2CH_3$ | 6-CHO | 91–93 |
| 11 | COOH | 6-$CF_3$ | 151–153 |
| 12 | CHO | 6-$NHCOC_4H_9$—t | 101–104 |
| 13 | $CO_2CH_3$ | 5-$N(CH_3)_2$ | 81–84 |
| 14 | $CO_2CH_2$—phenyl | 6-OCO—phenyl | 1.5746 |
| 15 | COOH | 6-OCO—phenyl | 132–134 |
| 16 | $CO_2CH_2$—phenyl | 6-$OCOCH_3$ | 1.5514 |
| 17 | COOH | 6-$OCOCH_3$ | 122–123 |
| 18 | COOH | 6-$OC_2H_4OC_2H_5$ | 105–107 |

TABLE 1-continued
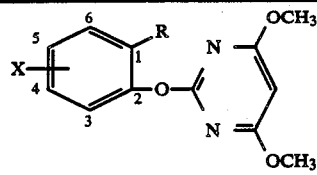
| Compound No. | R | X | Melting point (°C.) or refractive index $n_D^{20}$ |
|---|---|---|---|
| 19 | CO₂CH₂—(phenyl) | 6-OC₂H₄OC₂H₅ | 1.5563 |
| 20 | CHO | 6-OCH₂OCH₃ | 91–93 |
| 21 | COOH | 6-OCH₂OCH₃ | 101–103 |
| 22 | CO₂CH₂—(phenyl)—OCH₃ | 6-SCH₃ | 89–93 |
| 23 | CO₂C₂H₄CH(OC₂H₅)₂ | 6-SC₂H₅ | 1.5369 |
| 24 | CO₂CH₂—(phenyl) | 6-SCH₃ | 88–90 |
| 25 | COOH | 6-OCH₂—(phenyl) | 127–129 |
| 26 | CO₂CH₂—(phenyl) | 6-OCH₂—(phenyl) | 1.5809 |
| 27 | COOH | 6-OCH₂—(2-Cl-phenyl) | 141–143 |
| 28 | COOH | 6-OCH₂—(3-Cl-phenyl) | 117–120 |
| 29 | COOH·H₂O | 6-OCH₂—(4-Cl-phenyl) | 119–122 |
| 30 | CHO | 6-OCH(CH₃)—(phenyl) | 104–109 |
| 31 | COOH | 6-OCH(CH₃)—(phenyl) | 115–118 |

TABLE 1-continued

[Structure: X-substituted phenyl ring (positions 1-6 labeled, with R at position 1, O at position 2) connected via O-C(=N-)- to a 1,3-bis(methoxy)-2-aza group with OCH₃ groups and N atoms]

| Compound No. | R | X | Melting point (°C.) or refractive index $n_D^{20}$ |
|---|---|---|---|
| 32 | COOH | 6-OCH₂-(2,6-dichlorophenyl) | 142–144 |
| 33 | COOH | 6-OCH₂-(2,4-dimethylphenyl) | 143–144 |
| 34 | COOH | 6-OCH₂-(3,5-dimethylphenyl) | 122–117 |
| 35 | COOH | 6-OCH₂-(4-ethylphenyl) | 112–114 |
| 36 | CHO | 6-OCH₂-(4-ethylphenyl) | 92–94 |
| 37 | COOH | 6-OCHF₂ | 113–115 |
| 38 | COOH | 6-OCH₂C≡CH | 116–119 |
| 39 | CO₂CH₂-phenyl | 6-OC₃H₆OC₂H₅ | 1.5535 |
| 40 | COOH | 6-OC₃H₆OC₂H₅ | Not measurable |
| 41 | CHO | 6-OCH₂-phenyl | 107–110 |
| 42 | CHO | 6-OCHF₂ | 87–89 |
| 43 | CO₂CH₃ | 6-OCHF₂ | 1.5205 |
| 44 | CHO | 6-OCH₂C≡CH | 138–141 |
| 45 | CHO | 6-OCH₂CH═CH₂ | 110–111 |
| 46 | CO₂CH₃ | 3-CO₂H | 134–136 |
| 47 | CO₂CH₂-phenyl | 6-CO₂H | 168–174 |
| 48 | CO₂H | 6-NHCOC₄H₉—t | 192–195 |

TABLE 1-continued

[Structure: X-substituted phenyl ring (positions 1-6) with R at position 1, and position 2 connected via O-C(=N-OCH₃)(N=... with OCH₃ groups)]

| Compound No. | R | X | Melting point (°C.) or refractive index $n_D^{20}$ |
|---|---|---|---|
| 49 | CO₂CH₂-phenyl | 6-NHCO-phenyl | 73–76 |
| 50 | CO₂CH₃ | 3-CHO | 90–91 |
| 51 | CO₂CH₃ | 3-CO₂CH₃ | 108–110 |
| 52 | CHO | 6-OCH₂-(2,4-dimethylphenyl) | 155–160 |
| 53 | CHO | 6-OCH₂-(3,5-dimethylphenyl) | 93–97 |
| 54 | CHO | 6-OCH₂OCH₃ | 117–122 |
| 55 | CHO | 6-OCH₂-(2-chlorophenyl) | 135–138 |
| 56 | CHO | 6-OCH₂-(3-chlorophenyl) | 127–130 |
| 57 | CHO | 6-OCH₂-(4-chlorophenyl) | 147–150 |
| 58 | CO₂CH₃ | 6-OCH₂-(2-chlorophenyl) | 1.5675 |
| 59 | CHO | 6-OCH₂-(2,6-dichlorophenyl) | 130–135 |
| 60 | CO₂C₂H₄SO₂CH₃ | 6-OCH₂C≡CH | Not measurable |

TABLE 1-continued

[Structure: X-substituted phenyl ring (positions 3,4,5,6 with R at position 1 and O at position 2) connected via O to C(=N-)- with N linked to CH=CH groups bearing OCH₃ substituents]

| Compound No. | R | X | Melting point (°C.) or refractive index $n_D^{20}$ |
|---|---|---|---|
| 61 | $CO_2$–(phenyl) | 6-F | 94–95 |
| 62 | $CO_2CH_2CH=CH_2$ | 6-F | 1.5366 |
| 63 | $CO_2CH_2C\equiv CH$ | 6-F | 85–87 |
| 64 | $CO_2CH_2CH_2Cl$ | 6-F | 61–63 |
| 65 | $CO_2CH_2CF_3$ | 6-F | 106–107 |
| 66 | $CO_2$–(cyclohexyl) | 6-F | 1.5350 |
| 67 | $CO_2CH_2OCH_3$ | 6-F | 95–96 |
| 68 | $CO_2CH_2CH=CCl_2$ | 6-F | 1.5522 |
| 69 | $CO_2(CH_2)_3CH=CCl_2$ | 6-F | 1.5401 |
| 70 | $CO_2CH_2C\equiv CH$ | 6-Cl | 102–107 |
| 71 | $CO_2CH_2CF_3$ | 6-Cl | 1.5110 |
| 72 | $CO_2CH_2CH_2Cl$ | 6-Cl | 1.5421 |
| 73 | $CO_2CH_2CH_2OH$ | 6-Cl | 101–105 |
| 74 | $CO_2$–(cyclopentyl) | 6-Cl | 77–82 |
| 75 | $CO_2$–(cyclohexyl) | 6-Cl | 1.5420 |
| 76 | $CO_2CH_2$–(3-fluorophenyl) | 6-Cl | 77–82 |
| 77 | $CO_2CH_2OCH_3$ | 6-Cl | 1.5441 |
| 78 | $CO_2(CH_2)_2CH(OC_2H_5)_2$ | 6-Cl | 1.5129 |
| 79 | $CO_2CH_2CH_2CH=CH_2$ | 6-Cl | 1.5442 |
| 80 | $CO_2CH_2CH=CH_2$ | 6-Cl | 1.5485 |
| 81 | $CO_2$–(phenyl) | 6-Cl | 119–121 |
| 82 | $CO_2CH_2$–(4-methylphenyl) | 6-Cl | 75–77 |
| 83 | $CO_2CH_2$–(4-methoxyphenyl) | 6-Cl | 48–52 |

TABLE 1-continued

![structure header]

| Compound No. | R | X | Melting point (°C.) or refractive index $n_D^{20}$ |
|---|---|---|---|
| 84 | CO₂CH₂—⟨C₆H₄⟩—Cl (para) | 6-Cl | 101–105 |
| 85 | CO₂CH₂—⟨C₆H₄⟩—Cl (ortho) | 6-Cl | 97–98 |
| 86 | CO₂CH₂—⟨C₆H₄⟩—Cl (meta) | 6-Cl | 76–78 |
| 87 | CO₂CH₂—⟨C₆H₃⟩(Cl)(Cl) | 6-Cl | 105–106.5 |

The compounds of the present invention can be produced by the following processes, but their production is not restricted to such specific processes.

Process A

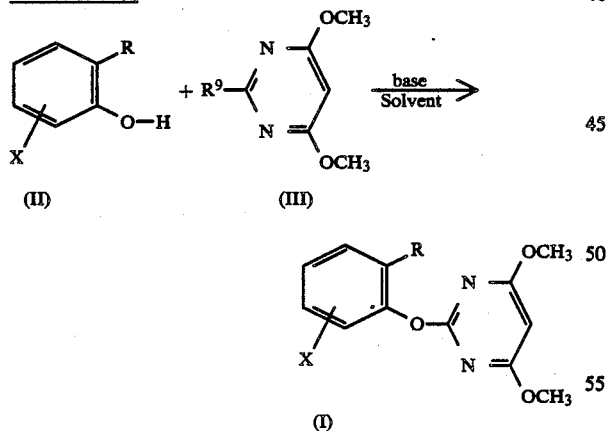

In the above formulas, R and X are as defined above, $R^9$ is a halogen atom, an alkylsulfonyl group or a benzylsulfonyl group which may be substituted.

The compound of the formula I of the present invention can be prepared by reacting the compound of the formula II and a pyrimidine compound of the formula III in the presence of a base, preferably in a solvent, within a temperature range from room temperature to the boiling point of the solvent for from 1 to 24 hours. In the absence of a solvent, the reaction can be conducted within a temperature range from 120° to 160° C. by using a carbonate of an alkali metal, such as anhydrous potassium carbonate.

Here, as the solvent, there may be employed a hydrocarbon solvent such as benzene, toluene or xylene, a halogenated hydrocarbon solvent such as dichloromethane or chloroform, an alcohol solvent such as methanol, ethanol or isopropanol, an ether solvent such as ethyl ether, isopropyl ether, tetrahydrofuran or 1,4-dioxane, a ketone solvent such as acetone or methyl ethyl ketone, an ester solvent such as methyl acetate or ethyl acetate, an aprotic polar solvent such as dimethylformamide, dimethylacetamide or dimethylsulfoxide, and others such as acetonitrile or water. As the base, there may be employed an alkali metal such as sodium metal or potassium metal, an alkali metal or alkaline earth metal hydride such as sodium hydride, potassium hydride or calcium hydride, a carbonate such as sodium carbonate or potassium carbonate, or a metal hydroxide such as sodium hydroxide or potassium hydroxide.

PROCESS B

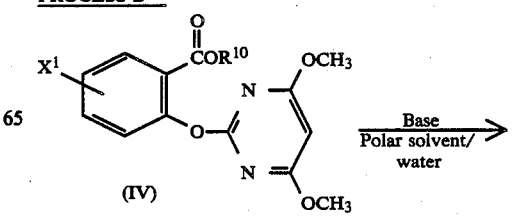

PROCESS B

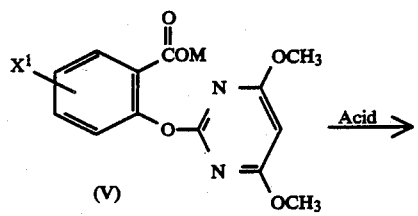

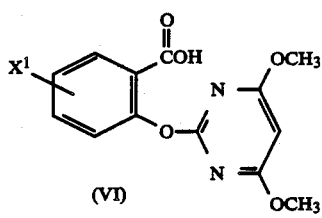

In the above formulas, $X^1$ is as defined above, $R^{10}$ is a lower alkyl group, a 2-(trimethylsilyl)ethyl group or a benzyl group, and M is an alkali metal or an alkaline earth metal.

Among the compounds of the present invention, those represented by the formula VI can be prepared by reacting the compound of the formula IV in the presence of a base in a polar solvent, in water or in a solvent mixture of a polar solvent and water within a temperature range from room temperature to the boiling point of the solvent for from 0.5 to 36 hours to obtain a compound of the formula V, which is then treated with an acid for precipitation to obtain a compound of the formula VI.

The solvent may be an alcohol solvent such as methanol, ethanol or isopropanol, or a ketone solvent such as acetone or methyl ethyl ketone. However, the solvent is not received to such examples. As the base, a carbonate such as sodium carbonate, potassium carbonate or calcium carbonate, or metal hydroxide such as sodium hydroxide or potassium hydroxide may be employed.

Further, when $R^{10}$ in the formula IV is a benzyl group, a compound of the formula VI can be obtained by the catalytic reduction by means of hydrogenation.

Further, when $R^{10}$ in the formula IV is a 2-(trimethylsilyl)ethyl group, a compound of the formula VI can be obtained by the reaction with tetra-n-butylammonium fluoride.

PROCESS C

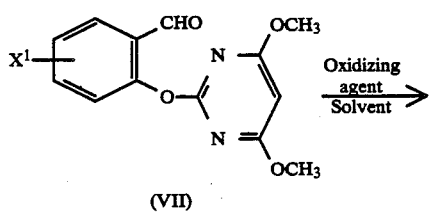

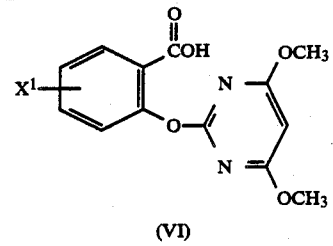

In the above formulas, $X^1$ is as defined above. Among the compounds of the present invention, the compound of the formula VI can be prepared by reacting the compound of the formula VII in the presence of an oxidizing agent in a polar solvent, in water or in a solvent mixture of a polar solvent and water within a temperature range of from cooling with ice to the boiling point of the solvent for from 0.5 to 24 hours.

The solvent may be a polar solvent such as water, acetone, t-butyl alcohol, acetic acid, pyridine or dioxane, or a solvent mixture of water and such a polar solvent. However, the solvent is not restricted to such specific examples. Further, as the oxidizing agent, oxygen, an aqueous hydrogen peroxide solution, chromic acid, silver oxide and a permanganate such as potassium permanganate, barium permanganate, calcium permanganate or magnecium permanganate may be used.

PROCESS D

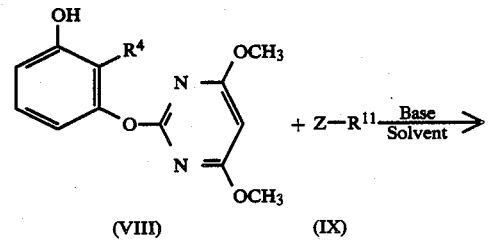

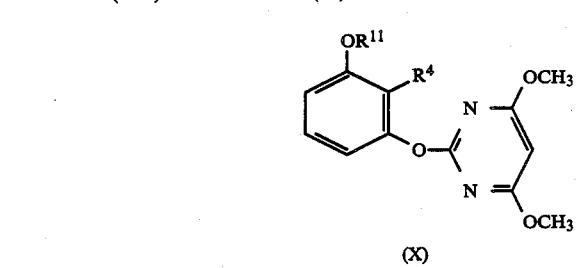

In the above formulas, $R^4$ is as defined above, and $R^{11}$ is an alkenyl group, an alkynyl group, an alkoxyalkyl group,

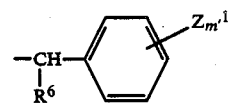

wherein $R^6$, $Z^1$ and $m'$ are as defined above, or $-COR^7$, wherein $R^7$ is an alkyl group or a phenyl group, and Z is a halogen atom.

Among the compounds of the present invention, the compound of the formula X can be prepared by reacting the compound of the formula VIII with the compound of the formula of the IX and the base in the presence of a solvent within a temperature range of from room temperature to the boiling point of the solvent for from 1 to 24 hours.

The solvent to be used here may be a hydrocarbon solvent such as benzene, toluene or xylene, a halogenated hydrocarbon solvent such as methylene chloride or chloroform, an ether solovent such as ethyl ether, isopropyl ether, tetrahydrofuran or 1,4-dioxane, a ketone solvent such as acetone or methyl ethyl ketone, an ester solvent such as methyl acetate or ethyl acetate, an aprotic polar solvent such as dimethylformamide, dimethylacetamide or dimethylsulfoxide, acetonitrile or water.

The base may be an alkali metal such as sodium metal or potassium metal, an alkali metal hydride or an alkaline earth metal hydride such as sodium hydride, potassium hydride or calcium hydride, a carbonate such as sodium carbonate, potassium carbonate, sodium hydrogencarbonate or potassium hydrogencarbonate, a metal hydroxide such as sodium hydroxide or potassium hydroxide, or an organic base such as triethylamine (tertiary amine) or pyridine.

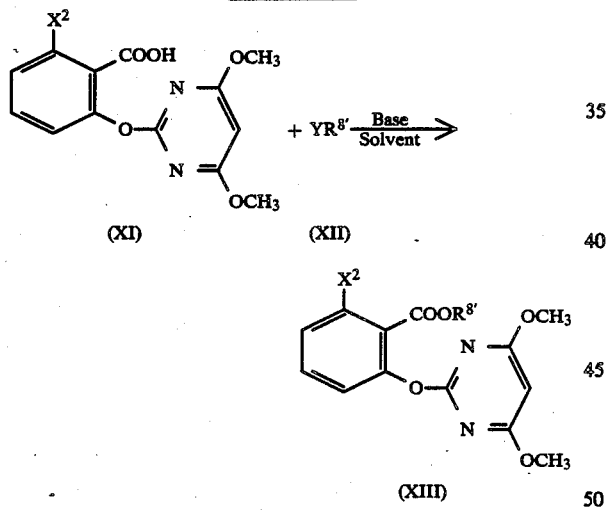

(XI) (XII) (XIII)

In the above formulas, $X^2$ is as defined above, $R^{8'}$ is $R^8$ less a phenyl group, and Y is a halogen atom.

Among the compounds of the present invention, the compound of the formula XIII can be prepared by reacting the compound of the formula XI with the compound of the formula XII in the presence of a base preferably in a solvent within a temperature range of from room temperature to the boiling point of the solvent for from 1 to 24 hours.

Here, the solvent may be a hydrocarbon solvent such as benzene, toluene or xylene, a halogenated hydrocarbon solvent such as dichloromethane or chloroform, an ether solvent such as ethyl ether, isopropyl ether, tetrahydrofuran or 1,4-dioxane, a ketone solvent such as acetone or methyl ethyl ketone, an ester solvent such as methyl acetate or ethyl acetate, an aprotic polar solvent such as dimethylformamide, dimethylacetamide or dimethylsulfoxide, acetonitrile or water.

The base may be an alkali metal such as sodium metal or potassium metal, an alkali metal hydride or an alkaline earth metal hydride such as sodium hydride, potassium hydride or calcium hydride, a carbonate such as sodium carbonate, potassium carbonate, sodium hydrogencarbonate or potassium hydrogencarbonate, a metal hydroxide such as sodium hydroxide or potassium hydroxide or an organic base such as trialkylamine or pyridine.

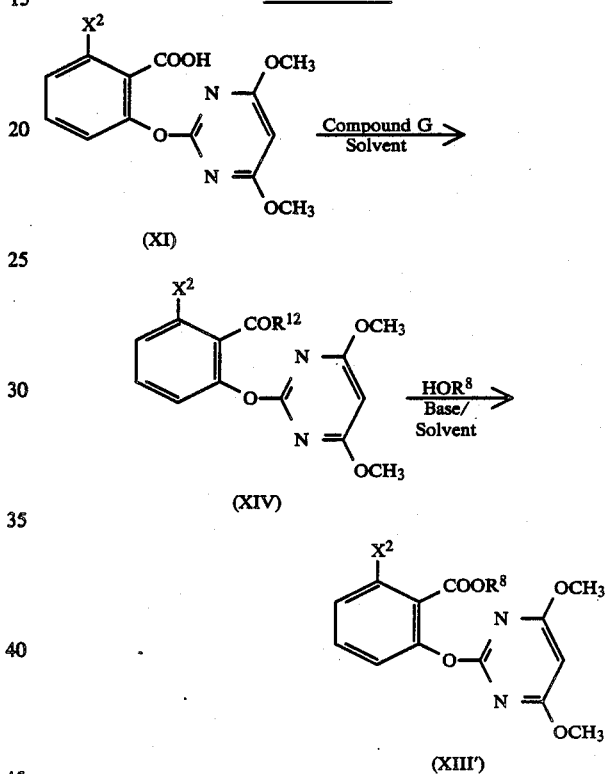

(XI) (XIV) (XIII')

In the above formulas, $R_8$ and $X^2$ are as defined above, and $R^{12}$ is an imidazolyl group or a chlorine atom.

The compound of the formula XIV can be obtained by reacting the compound of the formula XI with a compound G in a solvent within a temperature range of from room temperature to the boiling point of the solvent for from 1 to 12 hours. Here, the compound G may be, for example, carbonyldiimidazole, thionyl chloride, oxalic acid dichloride or phosgene. The solvent may be a hydrocarbon solvent such as benzene, toluene or xylene, a halogenated hydrocarbon solvent such as dichloromethane or chloroform, an ether solvent such as ethyl ether, isopropyl ether, tetrahydrofuran or 1,4-dioxane, a ketone solvent such as acetone, methyl ethyl ketone, and an ester solvent such as methyl acetate or ethyl acetate. However, the solvent is not restricted to these specific examples.

The compound of the formula XIV is reacted in a solvent, if necessary, by an addition of a base within a temperature range of from cooling with ice to room temperature, in some cases, at the boiling point of the solvent for from 0.5 to 12 hours to obtain the compound of the formula XIII' of the present invention. The solvent may be as mentioned above, and the base may also suitably be selected from organic amines and inorganic bases.

Now, the preparation of the compounds of the present invention will be described with reference to Examples. However, it should be understood that the present invention is by no means restricted by these specific Examples.

EXAMPLE 1

Preparation of methyl 2-(dimethoxy)methyl-6-(4,6-dimethoxypyrimidin-2-yl)oxy benzoate (Compound No. 2)

4,6-dimethoxy-2-methylsulfonylpyrimidine (4.8 g) was added to a suspension in dimethylformamide (20 ml) of methyl 6-(dimethoxy)methylsalicylate (4.5 g) and 35% potassium hydride (2.3 g), and the mixture was heated and stirred at a temperature of from 90° to 100° C. for 12 hours. The mixture was poured into a large amount of water and extracted with ethyl acetate. The extract was washed with water and dried. Then, the solvent was distilled off under reduced pressure. The residue thereby obtained was purified by silica gel column chromatography to obtain the above identified compound as white solid (4.4 g). Melting point: 83°–85° C.

EXAMPLE 2

Preparation of 4-methoxybenzyl 2-(4,6-dimethoxypyrimidin-2-yl)oxy-6-(methylthio)benzoate (Compound No. 22)

4-methoxybenzyl 6-(methylthio)salicylate (2.5 g), 4,6-dimethoxy-2-methylsulfonylpyrimidine (1.9 g) and potassium carbonate (2.3 g) were suspended in dimethylformamide (20 ml), and the suspension was heated and stirred at a temperature of from 120° to 130° C. for 4 hours. The reaction solution was poured into water and extracted with ethyl acetate. The extract was washed with water and dried. Then, the solvent was distilled off under reduced pressure. The residue thereby obtained was purified by silica gel column chromatography to obtain the above identified compound as white solid (3.0 g). Melting point: 89°–93° C.

EXAMPLE 3

Preparation of 5-(4,6-dimethoxypyrimidin-2-yl)oxy-1,3-benzodioxolane-4-carboxylic acid (Compound No. 7)

10% palladium charcoal (1.0 g), methyl alcohol (150 ml) and acetic acid (10 ml) were suspended, and benzyl 5-(4,6-dimethoxypyridine-2-yl)oxy-1,3-benzodioxolane-4-carboxylate (2.1 g) was added thereto. The catalytic reduction was conducted under atmospheric pressure. When absorption of hydrogen terminated, the catalyst was separated, and the filtrate was concentrated. The residue was dissolved in ethyl ether, washed with water, dried and concentrated to obtain the above identified compound as white solid (0.9 g). Melting point: 198°–201° C.

EXAMPLE 4

Preparation of 6-difluoromethoxy-2-(4,6-dimethoxypyrimidin-2-yl)oxy benzoic acid (Compound No. 37)

6-difluoromethoxy-2-(4,6-dimethoxypyrimidin-2-yl)oxybenzaldehyde (3 g) was dissolved in acetone (30 ml). Then, an equimolar amount of an aqueous potassium permanganate solution (10 ml) was dropwise added thereto. The mixture was stirred at room temperature for 3 hours. Then, the precipitate was filtered. A large amount of water was added to the filtrate, and unreacted material was removed by extraction with ethyl ether. The aqueous phase was acidified with a 5% hydrochloric acid aqueous solution, and extracted with ethyl ether. The extract was washed with water and dried. Then, ethyl ether was distilled off under reduced pressure to obtain the above identified compound as white crystals (1.9 g). Melting point: 113°–115° C.

EXAMPLE 5

Preparation of 6-(4,6-dimethoxypyrimidin-2-yl)oxy-2-(2,2-dimethylpropanoyl)amino benzoic acid (Compound No. 48)

6-(4,6-dimethoxypyridin-2-yl)oxy-2-(2,2-dimethylpropanoyl)amino benzaldehyde (1.1 g) was dissolved in acetone (30 ml). Then, equimolar amount of an aqueous potassium permanganate solution (10 ml) was dropwise added thereto. The mixture was stirred at room temperature of from 40° to 45° C. for 6 hours. Then, the precipitate was filtered. A large amount of water was added to the filtrate, and unreacted material was removed by extraction with ethyl ether. The aqueous phase was acidified with a 5% hydrochloric acid aqueous solution and extracted with ethyl ether. The extract was washed with water and dried. Then, ethyl ether was distilled off under reduced pressure to obtain the above identified compound as a slightly pink powder (1.0 g). Melting point: 192°–195° C.

EXAMPLE 6

Preparation of propargyl 2-(4,6-dimethoxypyrimidin-2-yl)oxy-6-fluorobenzoate (Compound No. 63)

2-(4,6-dimethoxypyrimidin-2-yl)oxy-6-fluorobenzoic acid (3.0 g) and carbonyldiimidazole (1.8 g) was dissolved in tetrahydrofuran (50 ml), and the solution was refluxed under heating for one hour. The reaction solution was cooled. Then, propargyl alcohol (2.0 g) and potassium carbonate (1.7 g) were added thereto, and the mixture was refluxed under heating for one hour. The mixture was poured into water and extracted with ethyl ether. The extract was washed with water and dried. Then, the solvent was distilled off, and the residue thereby obtained was purified by silica gel column chromatography to obtain propargyl 2-(4,6-dimethoxypyrimidin-2-yl)oxy-6-fluorobenzoate (1.8 g). Yield: 53%, white crystals, Melting point: 49°–50° C.

EXAMPLE 7

Preparation of allyl 2-chloro-6-(4,6-dimethoxypyrimidin-2-yl)oxy benzoate (Compound No. 80)

A suspension in dimethylformamide (10 ml) of 2-chloro-6-(4,6-dimethoxypyrimidin-2-yl)oxy benzoic acid (1.0 g), allyl bromide (0.5 g) and potassium carbonate (0.7 g) was heated and stirred at a temperature of from 100° to 110° C. for 30 minutes. The mixture was poured into water and extracted with ethyl acetate. The extract was washed with water and dried. Then, the solvent was distilled off, and the residue thereby obtained was purified by silica gel column chromatography to obtain allyl 6-chloro-2-(4,6-dimethoxypyrimidin-2-yl)oxy benzoate (0.6 g). Yield: 53.1%, colorless viscous liquid, refractive index $n_D^{20}$=1.5485.

EXAMPLE 8

Preparation of phenyl 2-chloro-6-(4,6-dimethoxypyrimidin-2-yl)oxy benzoate (Compound No. 81)

A suspension in dimethylformamide (20 ml) of 3.8 g of phenyl 6-chlorosalicylate (3.8 g), 4,6-dimethoxy-2-methylsulfonylpyrimidine (3.4 g) and potassium carbonate (2.1 g) was heated and stirred at a temperature of from 100° to 110° C. for 30 minutes. The mixture was poured into water and extracted with ethyl acetate. The extract was washed with water and dried. Then, the solvent was distilled off, and the residue thereby obtained was purified by silica gel column chromatography to obtain phenyl 2-chloro-6-(4,6-dimethoxypyrimidin-2-yl)oxy benzoate (2.5 g). Yield: 42%, white crystals, Melting point: 119°–121° C.

EXAMPLE 9

Preparation of methoxymethyl 2-chloro-6-(4,6-dimethoxypyrimidin-2-yl)oxy benzoate (Compound No. 77)

2-chloro-6-(4,6-dimethoxypyrimidin-2-yl)oxy benzoic acid (2.3 g), chloromethyl methyl ether (0.8 g) and potassium carbonate (1.2 g) were suspended in N,N-dimethylformamide (10 ml). This suspension was heated and stirred at 100° C. for one hour. After cooling, the solution was poured into a large amount of water, and the resulting oily substance was extracted with ethyl acetate. The organic layer was washed with water and dried. Then, the solvent was distilled off under reduced pressure. The residue was purified by column chromatography (n-hexane/ethyl acetate=9/1) to obtain a colorless viscous liquid (1.1 g). Refractive index $n_D^{20}$: 1.5441.

EXAMPLE 10

Preparation of 2-(4,6-dimethoxypyrimidin-2-yl)oxy-6-trifluoromethyl benzoic acid (Compound No. 11)

10% palladium charcoal (1.0 g), methyl alcohol (150 ml) and acetic acid (10 ml) were suspended, and then benzyl 2-(4,6-dimethoxypyrimidin-2-yl)oxy-6-trifluoromethyl benzoate (3.0 g) was added thereto. The catalytic reduction was conducted under atmospheric pressure. When absorption of hydrogen terminated, the catalyst was filtered off, and the filtrate was concentrated to about 70 ml. The reaction solution was poured into water and extracted with ethyl ether. The ethyl ether phase was washed with saturated sodium chloride aqueous solution and dried. Then, the solvent was distilled off under reduced pressure. The crystals thereby obtained were washed with isopropyl ether to obtain the above identified compound as white crystals (1.2 g). Melting point: 151°–153° C.

EXAMPLE 11

Preparation of 2-(4,6-dimethoxypyrimidin-2-yl)oxy-6-propargyloxy benzoic acid (Compound No. 38)

2-methylsulfonylethyl 2-(4,6-dimethoxypyrimidin-2-yl)oxy-6-propargyloxy benzoate (1.4 g, 3.2 mM) was dissolved in tetrahydrofuran (10 ml), and then a 2% sodium hydroxide aqueous solution (7.5 ml) was added thereto. The mixture was stirred at room temperature for two hours. Then, tetrahydrofuran was distilled off under reduced pressure, and the residue was neutralized with a 5% hydrochloric acid aqueous solution and extracted with ethyl acetate. The extract was dried over anhydrous sodium sulfate, and ethyl acetate was distilled off under reduced pressure to obtain crude crystals (1.0 g). These crystals were recrystallized from carbon tetrachloride to obtain slightly brown crystals (0.6 g). Melting point: 116°–119° C.

In a similar manner, 2-(4,6-dimethoxypyrimidin-2-yl)oxy-6-allyloxy benzoic acid was prepared. Melting point: 98°–101° C.

The herbicidal composition of the present invention comprises a herbicidally effective amount of a 2-phenoxypyrimidine derivative of the present invention and an agricultural carrier or adjuvant.

When the compound of the present invention is used as a herbicide, the compound may be used as it is or as formulated in various formulations such as a wettable powder, a granule, an emulsifiable concentrate or a dust by blending it with a carrier, a surfactant, a dispersing agent or an adjuvant which is commonly employed for the formulation of agricultural chemicals.

As the carrier to be used for the formulation, there may be mentioned a solid carrier such as jeeklite, talc, bentonite, clay, kaolin, diatomaceous earth, white carbon, vermiculite, slaked lime, silica sand, ammonium sulfate or urea, or a liquid carrier such as isopropyl alcohol, xylene, cyclohexane or methyl naphthalene. As the surfactant and dispersing agent, there may be mentioned, for example, an alcohol-sulfuric acid ester, an alkyl aryl sulfonate, lignin sulfonate, a polyoxyethylene glycol ether, a polyoxyethylene alkyl aryl ether or a polyoxyethylene sorbitol mono-alkylate. As the adjuvant, for example, carboxymethyl cellulose, polyethylene glycol or gum arabic may be mentioned. In practical use, such a herbicide may be diluted to a suitable concentration before application, or may directly be applied.

The herbicide of the present invention may be used in combination with other herbicides. Examples of such other herbicides will be given below.

1-(α,α-dimethylbenzyl)-3-p-tolylurea,
2-chloro-4,6-bis(ethylamino)-1,3,5-triazine,
2-chloro-4-ethylamino-6-isopropylamino-1,3,5-triazine,
2-chloro-4,6-bis(isopropylamino)-1,3,5-triazine,
2,4-bis(ethylamino)-6-methylthio-1,3,5-triazine,
2,4-bis(isopropylamino)-6-methylthio-1,3,5-triazine,
methyl α-(4,6-dimethoxypyrimidin-2-yl carbamoylsulfamoyl)-O-toluylate,
1-[2-(2-chloroethoxy)phenylsulfamoyl]-3-(4-methoxy-6-methyl-1,3,5-triazin-2-yl)urea,
2-(1-ethoxyiminobutyl)-5-(2-ethylthiopropyl-3-hydroxycyclohex-2-enone
methyl 3-(1-allyloxyaminobutylidene)-6,6-dimethyl-2,4-dioxocyclohexane carboxylate sodium salt,
4-(2,4-dichlorobenzoyl)-1,3-dimethyl-5-pyrazolyl-p-toluenesulfonate,
3-isopropyl-2,1,3-benzothiadiazinone-(4)-2,2-dioxide,
N-(1-ethylpropyl)-3,4-dimethyl-2,6-dinitroaniline,
α-(2-naphtoxy)propionanilide,
N-(phosphonomethyl)glycidylisopropylamine salt,
2-benzothiazol-2-yloxy-N-methylacetanilide,
2-chloro-2',6'-diethyl-N-(2-propoxyethyl)acetanilide,
2-chloro-2'-ethyl-N-(2-methoxy-1-methyl ethyl)-6'-methylacetanilide,
S-(2-methyl-1-piperidiylecarbonylmethyl)-O,O-di-n-propyldithiophosphate,
2-methylthio-4-ethylamino-6-isopropylamino-1,3,5-triazine.

The herbicide of the present invention is capable of controlling various weeds in a paddy field by irrigated soil treatment before or after the emergence of weeds or by foliage treatment. Further, the herbicide is capable of controlling various weeds in an upland field by soil treatment before or after the emergence of weeds or by foliage treatment.

The dose of the active ingredient varies depending upon the field to be treated i.e. whether it is an agricultural field or non-agricultural field, the type of treatment, i.e. whether it is soil treatment or foliage treatment, the crop plants to be protected and the weeds to be killed. However, it is usually within a range of from 0.1 to 1,000 g/10 a, preferably from 0.5 to 500 g/10 a.

For instance, for soil treatment for an upland agricultural field, the dose of the active ingredient is usually from 0.5 to 500 g/10 a, although it depends on the crop plant and weeds to be killed.

For foliage treatment for an upland agricultural field, the dose is usually from 0.1 to 500 g/10 a. In the case of a non-agricultural field, the dose is usually from 1 to 1,000 g/10 a for soil or foliage treatment.

Now, Formulation Examples for the herbicidal composition of the present invention will be given. However, it should be understood that the present invention is by no means restricted to these specific Examples. In these Examples, "%" means "% by weight".

FORMULATION EXAMPLE 1

(wettable powder)

10% of Compound No. 1, 0.5% of Emulgen 810 (trademark, Kao Corporation), 0.5% of Demol N (trademark, Kao Corporation), 20% of Kunilite 201 (trademark, Kunimine Kogyo K.K.) and 69% of Jeeklite CA (tradename, Jeeklite Company Ltd.) were uniformly mixed and pulverized to obtain a wettable powder.

FORMULATION EXAMPLE 2

(emulsifiable concentrate)

30% of Compound No. 5, 20% of cyclohexanone, 11% of polyoxyethylene alkyl aryl ether, 4% of calcium alkylbenzenesulfonate and 35% of methyl naphthalene, were uniformly dissolved to obtain an emulsifiable concentrate.

FORMULATION EXAMPLE 3

(granule)

5% of Compound No. 10, 2% of a sodium salt of a lauryl alcohol-sulfuric acid ester, 5% of sodium lignin sulfonate, 2% of carboxymethyl cellulose and 86% of clay were uniformly mixed and pulverized. To 100 parts by weight of this mixture, 20 parts by weight of water was added, and the mixture was kneaded, and granulated into granules of from 14 to 32 mesh by means of an extrusion granulating machine, followed by drying to obtain granules.

FORMULATION EXAMPLE 4

(dust)

2% of Compound No. 21, 5% of diatomaceous earth and 93% of clay were uniformly mixed and pulverized to obtain a dust.

The compounds and the herbicidal compositions of the present invention are capable of effectively controlling annual weeds such as barnyardgrass (*Echinochloa crus-galli*), flatsedge (*Cyperus difformis*), monochoria (*Monochoria varinalis*), bulrush (*Scirpul hotarui*) and *Alisma canaliculatum*, and perennial weeds such as *Cyperus serotinus, Sagittaria pygmaea* and *Eleocharis kuroguwai*, grown in paddy fields. Further, they are capable of effectively controlling annular weeds such as barnyardglass (*Echinochloa crus-galli*), crabgrass (*Digitaria sanguinalis*), goosegrass (*Elusine indica*), greenfoxtail (*Setaria viridis*), water foxtail (*Alopecurus aequalis*), annular bluegrass (*Poa annua*), wild oat (*Avena fatua*), italian ryegrass (*Lolium multiflorum*), smartweed (*Polygonum lapathifolium*), slender amaranth (*Amaranthus viridis*), lambsquarters (*Chenopodium album*), velvetleaf (*Abtilon theophrasti*), prickly sida (*Sida spinosa*), sicklepod (*Cassia tora*), chickweed (*Stellaria media*), morningglory (*Ipomoea spp*), common cocklebur (*Xanthium strumarium*), rice flatsedge (*Cyperus iria*), broadleaf signalgrass (*Brachiaria platyphylla*), itchgrass (*Rottoboellia exaltata*), down brome (*Bromus tectorum*), wild buckwheat (*Polygonum convolvulus*), wild mustard (*Brassica arvensis*) and devils baggartickes (*Bidens frondosa*), and perennial weeds such as purple nutsedge (*Cyperus rotundus*), johnsongrass (*Sorghum halepense*), bermudagrass (*Cyanodon dactylon*) and quackgrass (*Agropyron repens*) grown in upland fields. On the other hand, the safety to crop plants are high. Further, the compounds of the present invention have a feature that as compared with the known compounds disclosed in the afore-mentioned publications and literature, the effects against perennial weeds such as purple nutsedge and johnsongrass are superior.

Now, the herbicidal activities of the herbicides of the present invention will be described with reference to Test Examples.

TEST EXAMPLE 1

(soil treatment)

In a 100 cm² pot filled with soil, seeds of barynardgrass, crabgrass, smartweed, slender amarauth, lambsquarter and rice flatsedge were sown and covered with soil of a thickness of from 0.5 to 1 cm. One day layer from the seeding, a predetermined amount of a wettable powder prepared in accordance with Formulation Example 1, was diluted with water and applied to the soil surface at a rate of 100 liters per 10 ares (dose of active ingredient: 400 g/10 a). The evaluation was conducted on the 20th day after the treatment with the herbicide. The results were evaluated in accordance with the standards as identified in Table 2 and shown by the index numbers in Table 3.

TABLE 2

| Index No. | Herbicidal effects |
|---|---|
| 0 | No herbicidal effect |
| 1 | Herbicidal effect: more than 0% and less than 30% |
| 2 | Herbicidal effect: at least 30% and less than 50% |
| 3 | Herbicidal effect: at least 50% and less than 70% |
| 4 | Herbicidal effect: at least 70% and less than 90% |
| 5 | Herbicidal effect: more than 90% |

TABLE 3

| Compound No. | Herbicidal effects | | | | | |
|---|---|---|---|---|---|---|
| | Ech | Dig | Pol | Ama | Che | Cyi |
| 2 | — | — | 5 | 5 | 5 | 4 |
| 3 | — | — | 5 | 5 | 5 | 5 |
| 4 | — | — | 3 | 5 | 4 | 5 |
| 5 | — | — | 5 | 5 | 5 | 5 |
| 6 | — | — | 3 | 5 | 4 | 2 |
| 7 | — | — | 5 | 5 | 5 | 5 |
| 8 | — | — | 5 | 5 | 4 | 4 |
| 9 | — | — | 3 | 5 | 5 | 5 |
| 10 | — | — | 5 | 5 | 5 | 5 |
| 11 | — | — | 5 | 5 | 5 | 5 |
| 13 | — | — | 4 | 5 | 5 | 5 |
| 15 | — | — | 5 | 5 | 4 | 5 |
| 17 | — | — | 4 | 5 | 4 | 5 |
| 18 | — | — | 5 | 5 | 5 | 5 |
| 19 | — | — | 5 | 5 | 5 | 5 |
| 21 | — | — | 5 | 5 | 4 | 5 |
| 22 | — | — | 5 | 5 | 5 | 5 |
| 23 | — | — | 5 | 5 | 5 | 5 |
| 25 | — | — | 5 | 5 | 5 | 5 |
| 26 | — | — | 4 | 5 | 5 | 5 |
| 27 | — | — | 4 | 4 | 5 | 5 |
| 28 | — | — | 4 | 5 | 5 | 5 |
| 29 | — | — | 4 | 5 | 5 | 5 |
| 30 | — | — | 2 | 4 | 4 | 3 |
| 31 | — | — | 5 | 5 | 5 | 5 |
| 32 | — | — | 4 | 5 | 5 | 5 |
| 33 | — | — | 3 | 5 | 4 | 5 |
| 35 | — | — | 5 | 5 | 4 | 5 |
| 37 | — | — | 5 | 5 | 5 | 5 |
| 38 | — | — | 5 | 5 | 5 | 5 |
| 39 | — | — | 0 | 5 | 4 | 4 |
| 40 | — | — | 3 | 5 | 5 | 5 |
| 41 | — | — | 5 | 5 | 3 | 5 |
| 42 | — | — | 5 | 5 | 5 | 5 |
| 43 | — | — | 5 | 5 | 5 | 5 |
| 44 | — | — | 4 | 5 | 4 | 5 |
| 45 | — | — | 5 | 5 | 4 | 5 |
| 60 | — | — | 2 | 5 | 4 | 5 |
| 61 | 5 | 5 | 5 | 5 | 5 | 5 |
| 62 | 5 | 5 | 5 | 5 | 5 | 5 |
| 63 | 5 | 5 | 5 | 5 | 5 | 5 |
| 64 | 5 | 5 | 5 | 5 | 5 | 5 |
| 65 | 5 | 5 | 5 | 5 | 5 | 5 |
| 66 | 5 | 5 | 5 | 5 | 5 | 5 |
| 67 | 5 | 5 | 5 | 5 | 5 | 5 |
| 68 | 5 | 5 | 5 | 5 | 5 | 5 |
| 69 | 5 | 5 | 5 | 5 | 5 | 5 |
| 70 | 5 | 5 | 5 | 5 | 5 | 5 |
| 71 | 5 | 5 | 5 | 5 | 5 | 5 |
| 72 | 5 | 5 | 5 | 5 | 5 | 5 |
| 73 | 5 | 5 | 5 | 5 | 5 | 5 |
| 74 | 5 | 5 | 5 | 5 | 5 | 5 |
| 75 | 5 | 5 | 5 | 5 | 5 | 5 |
| 76 | 5 | 5 | 5 | 5 | 5 | 5 |
| 77 | 5 | 5 | 5 | 5 | 5 | 5 |
| 78 | 5 | 5 | 5 | 5 | 5 | 5 |
| 79 | 5 | 5 | 5 | 5 | 5 | 5 |
| 80 | 5 | 5 | 5 | 5 | 5 | 5 |
| 81 | 5 | 5 | 5 | 5 | 5 | 5 |
| 82 | 5 | 5 | 5 | 5 | 5 | 5 |
| 83 | 5 | 5 | 5 | 5 | 5 | 5 |
| 84 | 4 | 5 | 5 | 5 | 5 | 4 |
| 85 | 4 | 5 | 5 | 5 | 5 | 5 |
| 86 | 5 | 5 | 5 | 5 | 5 | 5 |
| 87 | 4 | 5 | 5 | 5 | 5 | 4 |
| Comparative Compound A | 0 | 0 | 0 | 0 | 0 | 5 |
| Comparative Compound B | 0 | 0 | 0 | 0 | 2 | 5 |
| Comparative Compound C | 0 | 0 | 0 | 0 | 0 | 0 |

Note 1. The abbreviations of the tested plants are as follows (the same abbreviations may be used in other Tables):
Ech: barnyardgrass (*Echinochloa crus-galli*)
Dig: crabgrass (*Digitaria sanguinalis*)
Pol: smartweed (*Polygonum lapathifolium*)
Ama: slender amaranth (*Amarathus viridis*)
Che: lambsquarters (*Chenopodium album*)
Cyi: rice flatsedge (*Cyperus iria*)

Note 2. Comparative Compounds A, B and C will be identified below (the same applies in other Tables): Comparative Compound A (disclosed in Japanese Unexamined Patent Publication No. 55729/1979)

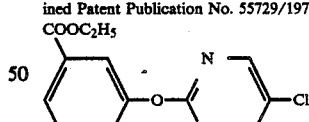

Comparative Compound B (disclosed in Japanese Unexamined Patent Publication No. 55729/1979)

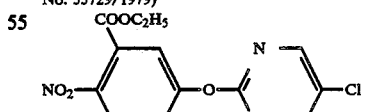

Comparative Compound C (disclosed in Arg. Biol. Chem., Vol. 30, No. 9,896 (1966))

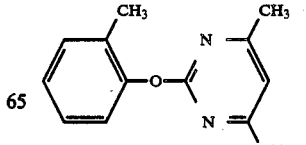

TEST EXAMPLE 2

(Foliage treatment)

In a 100 cm² pot filled with soil, seeds of barnyardgrass, crabgrass, smartweed, slender amaranth, lambsquarters and rice flatsedge, were sown, and covered with soil of a thickness of from 0.5 to 1 cm. The pot was cultured in a glass chamber at a temperature of from 20° to 25° C. for 2 weekts, and then a predetermined amount of a wettable powder prepared in accordance with Formulation Example 1 was diluted with water, and applied to the foligate at a rate of 100 liters per 10 ares (dose of active ingredient: 400 g/10a). The evaluation was conducted on 14th day after the treatment with the herbicide. The results were evaluated in accordance with the standards as identified in Table 2, and shown by the index numbers in Table 4.

TABLE 4

| Compound No. | Herbicidal effects |||||| 
|---|---|---|---|---|---|---|
| | Ech | Dig | Pol | Ama | Che | Cyi |
| 2 | 5 | — | 4 | 5 | 3 | 4 |
| 3 | 5 | — | 5 | 5 | 5 | 5 |
| 4 | 5 | — | 5 | 5 | 5 | 5 |
| 5 | 5 | — | 5 | 5 | 5 | 5 |
| 6 | 2 | — | 5 | 5 | 4 | 2 |
| 7 | 5 | — | 5 | 5 | 5 | 5 |
| 8 | 5 | — | 5 | 5 | — | 4 |
| 9 | 5 | — | 5 | 5 | 5 | 5 |
| 10 | 5 | — | 5 | 5 | 5 | 5 |
| 11 | 5 | — | 5 | 5 | 5 | 5 |
| 12 | 5 | — | 3 | 5 | 4 | 4 |
| 13 | 5 | — | 5 | 5 | 5 | 5 |
| 14 | 2 | — | 3 | 5 | 4 | 1 |
| 15 | 0 | — | 2 | 5 | 5 | 5 |
| 18 | 5 | — | 5 | 5 | 5 | 5 |
| 19 | 5 | — | 5 | 5 | 5 | 5 |
| 20 | 5 | — | 5 | 5 | 5 | 5 |
| 21 | 5 | — | 5 | 5 | 5 | 5 |
| 22 | 3 | — | 5 | 5 | 3 | 4 |
| 23 | 4 | — | 4 | 4 | 5 | 4 |
| 25 | 4 | — | 5 | 5 | 5 | 5 |
| 26 | 3 | — | 5 | 4 | 4 | 0 |
| 28 | 4 | — | 5 | 5 | 4 | 5 |
| 29 | 4 | — | 5 | 5 | 5 | 5 |
| 31 | 4 | — | 5 | 5 | 4 | 5 |
| 32 | 2 | — | 4 | 5 | 5 | 5 |
| 33 | 4 | — | 5 | 5 | 4 | 4 |
| 34 | 4 | — | 5 | 5 | 5 | 5 |
| 35 | 5 | — | 5 | 5 | 5 | 5 |
| 36 | 2 | — | 4 | 4 | 4 | 2 |
| 37 | 5 | — | 5 | 5 | 5 | 5 |
| 38 | 5 | — | 5 | 5 | 5 | 5 |
| 40 | 5 | — | 5 | 5 | 5 | 5 |
| 41 | 4 | — | 5 | 5 | 4 | 5 |
| 42 | 5 | — | 5 | 5 | 5 | 5 |
| 43 | 5 | — | 5 | 5 | 5 | 5 |
| 44 | 5 | — | 5 | 5 | 5 | 5 |
| 45 | 5 | — | 5 | 5 | 5 | 5 |
| 60 | 4 | — | 4 | 5 | 2 | 4 |
| 61 | 5 | 5 | 5 | 5 | 5 | 5 |
| 62 | 5 | 5 | 5 | 5 | 5 | 5 |
| 63 | 5 | 5 | 5 | 5 | 5 | 5 |
| 64 | 5 | 5 | 5 | 5 | 5 | 4 |
| 65 | 5 | 5 | 5 | 5 | 5 | 5 |
| 66 | 5 | 5 | 5 | 5 | 5 | 3 |
| 67 | 5 | 5 | 5 | 5 | 5 | 5 |
| 68 | 5 | 5 | 5 | 5 | 5 | 5 |
| 69 | 5 | 5 | 5 | 5 | 5 | 5 |
| 70 | 5 | 5 | 5 | 5 | 5 | 5 |
| 71 | 5 | 5 | 5 | 5 | 5 | 5 |
| 72 | 5 | 5 | 5 | 5 | 5 | 5 |
| 73 | 5 | 3 | 5 | 5 | 5 | 3 |
| 74 | 5 | 5 | 5 | 5 | 5 | 5 |
| 75 | 5 | 5 | 5 | 5 | 5 | 4 |
| 76 | 5 | 5 | 5 | 5 | 5 | 5 |
| 77 | 5 | 5 | 5 | 5 | 5 | 5 |
| 78 | 5 | 5 | 5 | 5 | 5 | 5 |
| 79 | 5 | 5 | 5 | 5 | 5 | 5 |
| 80 | 5 | 5 | 5 | 5 | 5 | 5 |
| 81 | 5 | 5 | 5 | 5 | 5 | 3 |
| 82 | 5 | 5 | 5 | 5 | 5 | 4 |
| 83 | 5 | 5 | 5 | 5 | 5 | 5 |
| 84 | 5 | 5 | 5 | 5 | 5 | 5 |
| 85 | 5 | 5 | 5 | 5 | 5 | 3 |
| 86 | 5 | 5 | 5 | 5 | 5 | 5 |
| 87 | 5 | 4 | 5 | 5 | 5 | 2 |
| Comparative Compound A | 0 | 1 | 2 | 2 | 0 | 5 |
| Comparative Compound B | 1 | 1 | 2 | 1 | 1 | 5 |
| Comparative Compound C | 1 | 1 | 1 | 1 | 1 | 1 |

TEST EXAMPLE 3

(effects against perennial weeds)

In a 600 cm² pot filled with soil, tubers of purple nutsedge and rhizomes of johnsongrass were planted and covered with soil of a thickness of from 0.5 to 1 cm. For the soil treatment, a predetermined amount of a wettable powder prepared in accordance with Formulation Example 1 was diluted with water and applied to the soil surface at a rate of 100 liters per 10 ares one day after the plantation. For the foliage treatment, the pot was cultured in a glass chamber at a temperature of from 20° to 25° C. for 2 weeks, and then a predetermined amount of a wettable powder prepared in accordance with Formulation Example 1 was diluted with water containing 2,000 ppm of surfactant wk as an extender and applied to the foliage at a rate of 100 liters per 10 ares. The evaluation was conducted on the 30th day after the treatment with the herbicide in the case of the soil treatment, and on the 21st day in the case of the foliage treatment. The results were evaluated in accordance with the standards as identified in Table 2 and shown by the index numbers in Table 5.

TABLE 5

| Compound No. | Dose of active ingredient (g/10a) | Soil Treatment || Foliage Treatment ||
|---|---|---|---|---|---|
| | | Cyr | Sor | Cyr | Sor |
| 3 | 400 | 5 | — | 4 | 5 |
| 5 | 400 | 3 | — | 5 | — |
| 7 | 400 | 5 | — | 5 | — |
| 11 | 400 | 5 | — | 5 | 5 |
| 18 | 400 | 5 | — | 5 | — |
| 19 | 400 | 4 | — | — | — |
| 20 | 400 | — | — | 4 | — |
| 21 | 400 | — | — | 5 | — |
| 25 | 400 | 5 | — | 3 | — |
| 37 | 400 | 5 | — | 5 | — |
| 38 | 400 | 5 | — | 5 | — |
| 42 | 400 | 5 | — | 5 | — |
| 44 | 400 | — | — | 4 | — |
| 45 | 400 | 5 | — | 5 | — |
| 61 | 400 | 5 | 5 | 5 | — |
| 62 | 400 | 5 | 5 | 5 | — |
| 63 | 400 | 5 | 5 | 5 | — |
| 64 | 400 | 4 | 5 | 5 | — |
| 65 | 400 | 5 | 5 | 5 | — |
| 66 | 400 | 5 | 5 | 4 | — |

TABLE 5-continued

| Compound No. | Dose of active ingredient (g/10a) | Soil Treatment Cyr | Soil Treatment Sor | Foliage Treatment Cyr | Foliage Treatment Sor |
|---|---|---|---|---|---|
| 67 | 400 | 5 | 5 | 5 | — |
| 68 | 400 | 5 | 5 | 5 | — |
| 69 | 400 | 5 | — | 5 | — |
| 70 | 400 | 4 | 5 | 5 | — |
| 71 | 400 | 1 | 5 | 5 | 5 |
| 72 | 400 | 1 | 5 | 5 | 5 |
| 73 | 400 | 1 | 5 | 5 | — |
| 74 | 400 | 3 | — | 4 | — |
| 75 | 400 | 3 | — | — | — |
| 76 | 400 | 5 | — | 4 | — |
| 77 | 400 | 5 | — | 5 | — |
| 78 | 400 | 5 | — | 5 | — |
| 79 | 400 | 5 | — | 5 | — |
| 80 | 400 | 5 | 5 | 5 | 5 |
| 81 | 400 | 2 | 5 | 4 | 5 |
| 82 | 400 | 4 | 5 | 5 | 5 |
| 83 | 400 | 5 | 5 | 5 | 5 |
| 84 | 400 | — | — | 5 | 5 |
| 85 | 400 | 3 | 5 | 5 | 5 |
| 86 | 400 | 4 | 5 | 5 | 5 |
| 87 | 400 | 1 | 5 | 5 | 5 |
| Comparative Compound A | 400 | 0 | 0 | 0 | 0 |
| B | 400 | 0 | 0 | 0 | 0 |
| C | 400 | 0 | 0 | 0 | 0 |

Note 1. The abbreviations of the tested plants are as follows (the same abbreviations are used in other tables).
Cyr: purple nutsedge (*Cyperus rotundus*)
Sor: johnsongrass (*Sorghum halepense*)

TEST EXAMPLE 4

(safety to crop plants)

In 600 cm² pots filled with soil, seeds of barnyardgrass, greenfoxtail, smartweed, slender amaranth, water foxtail, lambsquarters, soybean, cotton and wheat were sown, tubers of purple nutsedge and rhizomes of johnsongrass were planted, and they were covered with soil of a thickness of from 0.5 to 1 cm. A predetermined amount of a wettable powder prepared in accordance with Formulation Example 1 was diluted with water and applied to the soil surface at a rate of 100 liters per 10 ares one day after the plantation. The evaluation was conducted on the 30th day after the treatment with the herbicide. The evaluation of the herbicidal effects was conducted in accordance with the standards as identified in Table 2, and the evaluation of phytotoxicity was conducted in accordance with the standards as identified in Table 6. The results are shown by the index numbers in Tables 7, 8 and 9.

TABLE 6

| Index | Phytotoxicity |
|---|---|
| 0 | No phytotoxicity |
| 1 | Phytotoxicity more than 0% and less than 30% |
| 2 | Phytotoxicity at least 30% and less than 50% |
| 3 | Phytotoxicity at least 50% and less than 70% |
| 4 | Phytotoxicity at least 70% and less than 90% |
| 5 | Phytotoxicity at least 90% to completely withered |

TABLE 7

| Compound No. | Dose of active ingredient (g/10a) | Phytotoxicity Gly | Phytotoxicity Gos | Herbicidal effect Ech | Herbicidal effect Set | Herbicidal effect Pol | Herbicidal effect Ama | Herbicidal effect Cyr |
|---|---|---|---|---|---|---|---|---|
| 45 | 25 | 1 | 1 | 4 | 4 | 5 | 5 | 5 |
| Comparative compound A | 25 | 0 | 0 | 0 | 0 | 0 | 0 | 0 |
| Comparative compound B | 25 | 0 | 0 | 0 | 0 | 0 | 0 | 0 |
| Comparative compound C | 25 | 0 | 0 | 0 | 0 | 0 | 0 | 0 |
| Comparative compound D | 25 | 0 | 0 | 0 | 0 | 0 | 0 | 0 |

Note 1. Comparative Compound D (disclosed in Japanese Unexamined Patent Publication No. 55729/1979)

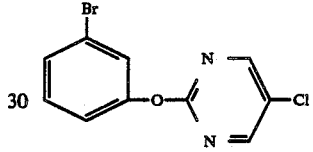

Note 2. Abbreviations for the tested plants are as follows:
Gly: soybean (*Glycine max*)
Gos: cotton (*Gossypium hirsutum*)
Set: greenfoxtail (*Setaria viridis*)

TABLE 8

| Compound No. | Dose of active ingredient (g/10a) | Phytotoxicity Tri | Herbicidal effects Alo | Herbicidal effects Pol | Herbicidal effects Ama | Herbicidal effects Che |
|---|---|---|---|---|---|---|
| 7 | 25 | 1 | 3 | 4 | 5 | 5 |
| 19 | 25 | 0 | 5 | 5 | 5 | 4 |
| 25 | 25 | 0 | 5 | 5 | 5 | 5 |
| 42 | 25 | 1 | 5 | 5 | 5 | 5 |
| 38 | 25 | 1 | 5 | 5 | 5 | 5 |
| Comparative Compound D | 25 | 0 | 0 | 0 | 0 | 0 |

Note: Abbreviations for the tested plants are as follows.
Tri: wheat (*Triticum aestivum*)
Alo: water foxtail (*Alopecurus aequalis*)

TABLE 9

| Compound No. | Dose of active ingredient (g/10a) | Phytotoxicity Gos | Herbicidal effects Ech | Herbicidal effects Pol | Herbicidal effects Cyr | Herbicidal effects Sor |
|---|---|---|---|---|---|---|
| 61 | 6.3 | 1 | 4 | 5 | 1 | 5 |
| 66 | 100 | 1 | 4 | 5 | 5 | 5 |
| " | 25 | 0 | 1 | 5 | 4 | 4 |
| 67 | 6.3 | 1 | 5 | 5 | 0 | 5 |
| " | 1.6 | 1 | 3 | 5 | 0 | 4 |
| 68 | 25 | 2 | 5 | 5 | 2 | 5 |
| " | 6.3 | 0 | 5 | 5 | 0 | 4 |
| 70 | 25 | 1 | 5 | 5 | 1 | 5 |
| " | 6.3 | 0 | 2 | 5 | 0 | 4 |
| 71 | 100 | 2 | 2 | 5 | 0 | 4 |
| " | 25 | 1 | 4 | 5 | 0 | 5 |
| 72 | 100 | 0 | 5 | 5 | 0 | 4 |
| " | 25 | 0 | 1 | 5 | 0 | 3 |
| 73 | 100 | 0 | 3 | 5 | 0 | 4 |
| 76 | 100 | 0 | 5 | 5 | 4 | 5 |

TABLE 9-continued

| Compound No. | Dose of active ingredient (g/10a) | Phyto-toxicity Gos | Herbicidal effects | | | |
|---|---|---|---|---|---|---|
| | | | Ech | Pol | Cyr | Sor |
| " | 25 | 0 | 5 | 5 | 1 | 5 |
| 77 | 6.3 | 1 | 5 | 5 | 1 | 5 |
| " | 1.6 | 0 | 5 | 5 | 0 | 5 |
| 78 | 6.3 | 1 | 4 | 5 | 3 | 5 |
| " | 1.6 | 0 | 4 | 5 | 3 | 4 |
| 79 | 100 | 1 | 5 | 5 | 5 | 5 |
| " | 25 | 1 | 5 | 5 | 5 | 5 |
| 84 | 100 | 1 | 5 | 5 | 2 | 5 |
| " | 25 | 0 | 5 | 5 | 0 | 5 |
| 85 | 100 | 0 | 5 | 5 | 3 | 5 |
| 86 | 100 | 0 | 5 | 5 | 2 | 5 |
| " | 25 | 0 | 4 | 5 | 0 | 5 |
| 87 | 100 | 0 | 2 | 5 | 0 | 4 |
| Comparative Compound A | 100 | 0 | 0 | 0 | 0 | 0 |
| B | 100 | 0 | 0 | 0 | 0 | 0 |
| C | 100 | 0 | 0 | 0 | 0 | 0 |

TEST EXAMPLE 5
(herbicidal effects against paddy field weeds)

In a 100 cm² pot, paddy field soil was filled and paddled, a seeds of barnyardgrass, unbrellaplant, monochoria and bulrush were sown. Then, water was introduced to a depth of 5 cm. Two days after the ceeding, a wettable powder prepared in accordance with Formulation Example 1 was diluted with water and dropwise added to the water surface so that 100 g of the active ingredient per 10 ares was applied. The evaluation was conducted on the 21st day after the application in accordance with the standards as identified in Table 2. The results are shown by the index numbers in Table 10.

TABLE 10

| Compound No. | Herbicidal effects | | | |
|---|---|---|---|---|
| | Ech | Cyp | Mon | Sci |
| 3 | 5 | 5 | 5 | 5 |
| 4 | 5 | 5 | 5 | 4 |
| 5 | 5 | 5 | 5 | 5 |
| 7 | 5 | 5 | 5 | 5 |
| 9 | 4 | 5 | 5 | 4 |
| 10 | 5 | 4 | 5 | 5 |
| 11 | 5 | 5 | 5 | 5 |
| 12 | 5 | 5 | 5 | 3 |
| 13 | 5 | 5 | 5 | 5 |
| 15 | 4 | 5 | 5 | 5 |
| 17 | 5 | 5 | 5 | 5 |
| 18 | 5 | 5 | 5 | 5 |
| 19 | 5 | 5 | 5 | 5 |
| 20 | 5 | 5 | 5 | 4 |
| 21 | 5 | 5 | 5 | 5 |
| 22 | 5 | 5 | 5 | 5 |
| 23 | 5 | 5 | 5 | 5 |
| 24 | 5 | 4 | 5 | 5 |
| 25 | 4 | 5 | 5 | 5 |
| 27 | 4 | 5 | 5 | 5 |
| 28 | 4 | 5 | 5 | 5 |
| 29 | 4 | 5 | 5 | 5 |
| 31 | 4 | 5 | 5 | 5 |
| 32 | 4 | 5 | 5 | 5 |
| 33 | 5 | 5 | 5 | 5 |
| 34 | 4 | 5 | 5 | 5 |
| 35 | 5 | 5 | 5 | 5 |
| 36 | 4 | 5 | 5 | 5 |
| 37 | 5 | 5 | 5 | 5 |
| 38 | 5 | 5 | 5 | 5 |
| 40 | 5 | 5 | 5 | 5 |
| 41 | 4 | 4 | 5 | 5 |
| 42 | 5 | 5 | 5 | 5 |
| 43 | 4 | 4 | 5 | 5 |

TABLE 10-continued

| Compound No. | Herbicidal effects | | | |
|---|---|---|---|---|
| | Ech | Cyp | Mon | Sci |
| 44 | 5 | 5 | 5 | 5 |
| 45 | 5 | 5 | 5 | 5 |
| 49 | 4 | 5 | 5 | 4 |
| Comparative Compound A | 0 | 3 | 0 | 1 |
| B | 0 | 5 | 0 | 1 |
| C | 0 | 0 | 0 | 0 |

Note: Abbreviations for the tested plants are as follows.
Cyp: unbrellaplant (*Cyperus difformis*)
Mon: monochoria (*Monochoria vaginalis*)
Sci: bulrush (*Scirpus Hotarui*)

We claim:

1. A 2-phenoxypyrimidine derivative having the formula:

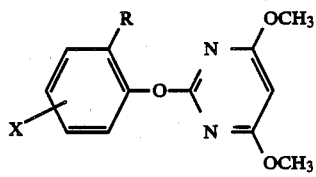

wherein R is a formyl group or —COOR¹, wherein R¹ is a hydrogen atom, a lower alkyl group, a 2-methylsulfonylethyl group, a diethoxypropyl group, a lower alkenyl group, a lower alkynyl group, a lower haloalkyl group, a lower haloalkenyl group, a lower alkoxyalkyl group, a lower hydroxyalkyl group, a $C_3$–$C_6$-cycloalkyl group, a phenyl group or a group of the formula:

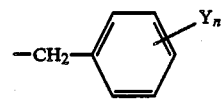

wherein Y is a halogen atom, a methyl group or a methoxy group and n is 0, 1 or 2; and X is a lower alkynyloxy group, a lower alkenyloxy group, a lower alkylthio group, a lower alkoxyalkyloxy group, a lower haloalkoxy group, an acetyloxy group, a benzoyloxy group, a trifluoromethyl group, a lower alkoxycarbonyl group, a lower dialkylamino group, a dimethoxymethyl group, or a group of the formula:

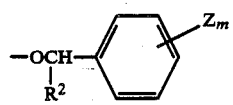

wherein R² is hydrogen atom or a methyl group, Z is a chlorine atom or a lower alkyl group and m is 0, 1, or 2, or

wherein R³ is a lower alkyl group or a phenyl group; or X forms a methylenedioxy group attached to the adjacent carbon atoms.

2. The 2-phenoxypyrimidine derivative according to claim 1, which has the formula:

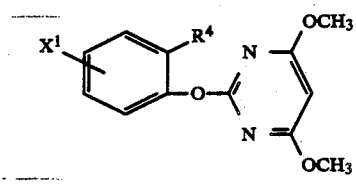

wherein $R^4$ is a formyl group or $-COOR^5$, wherein $R^5$ is a hydrogen atom, a lower alkyl group, a benzyl group which is unsubstituted or substituted by a methoxy group, a 2-methylsulfonylethyl group or a diethoxypropyl group; and $X^1$ is a lower alkynyloxy group, a lower alkenyloxy group, a lower alkylthio group, a lower alkoxyalkoxy group, a lower haloalkoxy group, an acetyloxy group, a benzoyloxy group, a trifluoromethyl group, a lower alkoxycarbonyl group, and a group of the formula:

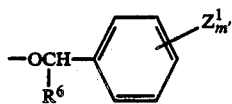

wherein $R^6$ is a hydrogen atom or a methyl group, $Z^1$ is a chlorine atom or a lower alkyl group and m' is 0, 1 or 2, a lower dialkylamino group,

wherein $R^3$ is a lower alkyl group or a phenyl group, or a dimethoxymethyl group, or $X^1$ forms a methylenedioxy group attached to the adjacent carbon atoms.

3. The 2-phenoxypyrimidine derivative according to claim 2, wherein $R^4$ is a formyl group or $-COOR^5$ wherein $R^5$ is a hydrogen atom, a lower alkyl group or a benzyl group.

4. The 2-phenoxypyrimidine derivative according to claim 2, wherein $X^1$ is an alkynyloxy group, an alkenyloxy group, an alkoxyalkoxy group, a haloalkoxy group, a benzoyloxy group, a trifluoromethyl group, an alkoxycarbonyl group, a dialkylamino group or

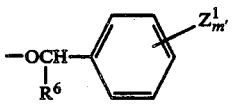

wherein $R^6$ is a hydrogen atom or a methyl group, $Z^1$ is an alkyl group and m' is 0 or 1, or $X^1$ forms a methylenedioxy group attached to the adjacent carbon atoms.

5. The 2-phenoxypyrimidine derivative according to claim 2, wherein $R^4$ is a formyl group or $-COOR^5$ wherein $R^5$ is a hydrogen atom or a benzyl group.

6. The 2-phenoxypyrimidine derivative according to claim 2, wherein $X^1$ is an alkynyloxy group, an alkenyloxy group, an alkoxyalkoxy group, a haloalkoxy group, a trifluoromethyl group, an alkoxycarbonyl group or a benzyloxy group, or $X^1$ forms a methylenedioxy group attached to the two adjacent carbon atoms.

7. The 2-phenoxypyrimidine derivative according to claim 2, wherein $R^4$ is a formyl group or $-COOR^5$ wherein $R^5$ is a hydrogen atom or a benzyl group, and $X^1$ is an alkynyloxy group, an alkenyloxy group, an alkoxyalkoxy group, a haloalkoxy group, a trifluoromethyl group, an alkoxycarbonyl group or a benzyloxy group, or $X^1$ forms a methylenedioxy group attached to the two adjacent carbon atoms.

8. The 2-phenoxypyrimidine derivative according to claim 2, wherein $R^4$ is a formyl group or $-COOR^5$ wherein $R^5$ is a hydrogen atom or a benzyl group, and $X^1$ is a $C_3-C_6$ alkynyloxy group, a $C_3-C_6$ alkenyloxy group, a $C_1-C_6$ alkoxy-$C_2-C_6$ alkoxy group, a $C_1-C_6$ haloalkoxy group, a trifluoromethyl group, a $C_1-C_6$ alkoxycarbonyl group for a benzyloxy group, or $X^1$ forms a methylenedioxy group attached to the two adjacent carbon atoms.

9. The 2-phenoxypyrimidine derivative according to claim 2, wherein $R^4$ is a formyl group or $-COOR^5$ wherein $R^5$ is a hydrogen atom or a benzyl group, and $X^1$ is a propynyloxy group, a propenyloxy group, an ethoxyethoxy group, a trifluoromethyl group, a difluoromethyl group, a methoxycarbonyl group or a benzyloxy group, or $X^1$ forms a methylenedioxy group attached to the two adjacent carbon atoms.

10. A herbicidal composition comprising a herbicidally effective amount of a 2-phenoxypyrimidine derivative as defined in claim 1 and an agricultural adjuvant.

11. The 2-phenoxypyrimidine derivative according to claim 1, wherein R is $-COOH$ and X is 6-trifluoromethyl.

12. The 2-phenoxypyrimidine derivative according to claim 1, wherein R is $-COOH$ and X is $6-OCH_2C\equiv CH$.

13. The 2-phenoxypyrimidine derivative according to claim 1, wherein R is a moiety of the formula:

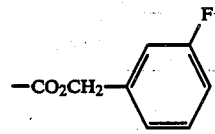

and X is 6-chloro.

14. The 2-phenoxypyrimidine derivative according to claim 1, wherein R is $-CO_2CH_2OCH_3$ and X is 6-chloro.

15. The 2-phenoxypyrimidine derivative according to claim 1, wherein R is a moiety of the formula:

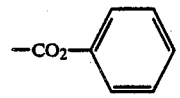

and X is 6-chloro.

16. The 2-phenoxypyrimidine derivative according to claim 1, wherein R is a moiety of the formula:

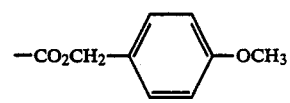

and X is 6-chloro.

* * * * *

UNITED STATES PATENT AND TRADEMARK OFFICE
CERTIFICATE OF CORRECTION

PATENT NO. :       4,889,552
DATED      :       Dec. 26, 1989
INVENTOR(S) :      Nobuhide Wada, et al It is certified that error appears in the above-identified patent and that said Letters Patent is hereby corrected as shown below:

The title is incorrectly recorded,
"2-PHENOXYPYRIMIDINE DERIVATIVE AND HERBIDICAL COMPOSITION"
should be:
--2-PHENOXYPYRIMIDINE DERIVATIVE AND HERBICIDAL COMPOSITION--

The Foreign Application Priority Data is incorrectly recorded,
" Apr. 14, 1987 [JP] Japan.....62-091787
  Apr. 14, 1988 [JP] Japan.....63-091788" should be:

--Apr. 14, 1987 [JP] Japan.....62-091787
   Apr. 14, 1987 [JP[ Japan.....62-091788--

Signed and Sealed this

Twentieth Day of November, 1990

Attest:

HARRY F. MANBECK, JR.

Attesting Officer      Commissioner of Patents and Trademarks